US009498179B1

United States Patent
Sen Sharma et al.

(10) Patent No.: US 9,498,179 B1
(45) Date of Patent: Nov. 22, 2016

(54) METHODS AND SYSTEMS FOR METAL ARTIFACT REDUCTION IN SPECTRAL CT IMAGING

(71) Applicant: General Electric Company, Schenectady, NY (US)

(72) Inventors: Kriti Sen Sharma, Woburn, MA (US); Hewei Gao, Pewaukee, WI (US); Debashish Pal, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 56 days.

(21) Appl. No.: 14/706,759

(22) Filed: May 7, 2015

(51) Int. Cl.
*A61B 6/00* (2006.01)
*A61B 6/03* (2006.01)
*G06T 11/00* (2006.01)

(52) U.S. Cl.
CPC ............ *A61B 6/5258* (2013.01); *A61B 6/032* (2013.01); *A61B 6/461* (2013.01); *A61B 6/482* (2013.01); *G06T 11/008* (2013.01); *G06T 2207/10081* (2013.01)

(58) Field of Classification Search
CPC .. A61B 6/482; A61B 6/5252; A61B 6/5258; G06T 5/002; G06T 11/008; G06T 2207/10081; G06T 2211/408
See application file for complete search history.

(56) References Cited

U.S. PATENT DOCUMENTS

| | | | |
|---|---|---|---|
| 8,503,750 B2 | 8/2013 | Benson et al. | 382/131 |
| 2010/0054569 A1* | 3/2010 | Bruder et al. | 382/131 |
| 2011/0007956 A1* | 1/2011 | Meyer et al. | 382/131 |
| 2014/0056497 A1* | 2/2014 | Hsieh et al. | 382/131 |
| 2015/0146955 A1* | 5/2015 | Dong et al. | G06T 11/003 382/131 |
| 2016/0117850 A1* | 4/2016 | Jin et al. | G06T 11/008 382/131 |

OTHER PUBLICATIONS

Kalender, W. et al., "Reduction of CT Artifacts Caused by Metallic Implants," Radiology, vol. 164, No. 2, Aug. 1987, 2 pages.
Meyer, E. et al., "Normalized Metal Artifact Reduction (NMAR) in Computed Tomography," Medical Physics, vol. 37, No. 10, Oct. 2010, 12 pages.
Bamberg, F. et al., "Metal Artifact Reduction by Dual Energy Computed Tomography Using Monoenergetic Extrapolation," European Radiology, vol. 21, No. 7, Jul. 2011, Published Online Jan. 20, 2011, 6 pages.
Zhao, C. et al., "Monoenergetic Imaging of Dual-Energy CT Reduces Artifacts from Implanted Metal Orthopedic Devices in Patients with Factures," Academic Radiology, vol. 18, No. 10, Oct. 2011, 6 pages.
Lee, Y. et al., "Metal Artefact Reduction in Gemstone Spectral Imaging Dual-Energy CT With and Without Metal Artefact Reduction Software," European Radiology, vol. 22, No. 6, Jun. 2012, Published Online Feb. 4, 2012, 10 pages.

(Continued)

*Primary Examiner* — Andrew W Johns
(74) *Attorney, Agent, or Firm* — Alleman Hall McCoy Russell & Tuttle LLP

(57) ABSTRACT

Various methods and systems for spectral computed tomography imaging are provided. In one embodiment, a method comprises acquiring a first projection dataset and a second projection dataset, detecting a location of metal in the first projection dataset, applying corrections to the first and second projection datasets based on the location of the metal, and displaying an image reconstructed from the corrected first and second projection datasets. In this way, metal artifacts may be substantially reduced in dual or multi-energy CT imaging.

20 Claims, 9 Drawing Sheets

(56) References Cited

OTHER PUBLICATIONS

Pal, D. et al., "Metal Artifact Correction Algorithm for CT," 2013 IEEE Nuclear Science Symposium and Medical Imaging Conference (NSS/MIC), Oct. 27, 2013, 3 pages.

Gao, Hewei et al., "Methods and Systems for Spectral CT Imaging," U.S. Appl. No. 14/567,828, filed Dec. 11, 2014, 26 pages.

Pal, D. et al., "Metal Artifact Correction Algorithm for CT," 2013 IEEE Nuclear Science Symposium and Medical Imaging Conference (NSS/MIC), Oct. 27, 2013, 4 pages.

* cited by examiner

METHODS AND SYSTEMS FOR METAL ARTIFACT REDUCTION IN SPECTRAL CT IMAGING

FIELD

Embodiments of the subject matter disclosed herein relate to diagnostic imaging, and more particularly, to metal artifact reduction for dual energy spectral computed tomography (CT) imaging.

BACKGROUND

Dual or multi-energy spectral computed tomography (CT) systems can reveal the densities of different materials in an object and generate images acquired at multiple monochromatic x-ray energy levels. In the absence of object scatter, a system derives the behavior at a different energy based on a signal from two regions of photon energy in the spectrum: the low-energy and the high-energy portions of the incident x-ray spectrum. In a given energy region of medical CT, two physical processes dominate the x-ray attenuation: Compton scattering and the photoelectric effect. The detected signals from two energy regions provide sufficient information to resolve the energy dependence of the material being imaged. Detected signals from the two energy regions provide sufficient information to determine the relative composition of an object composed of two hypothetical materials.

In some cases, the presence of metal (e.g., in the form of metal implants, dental fillings, and so on) may interfere with the x-ray attenuation, thereby causing metal artifacts in reconstructed images. For single energy acquisition, there are known metal artifact reduction algorithms which effectively reduce the presence of metal artifacts in the reconstructed image.

However, a simple application of known metal artifact reduction algorithms to dual energy CT leads to additional image artifacts. For example, a metal artifact reduction algorithm known to work well for single energy acquisition may be applied independently to both the high and the low channels in dual energy CT. As a result, different amounts of metal correction may occur in each channel. Material decomposition utilizes data from both channels, and new artifacts arise due to the inconsistency of metal correction between the channels.

BRIEF DESCRIPTION

In one embodiment, a method comprises acquiring a first projection dataset and a second projection dataset, detecting a location of metal in the first projection dataset, applying corrections to the first and second projection datasets based on the location of the metal, and displaying an image reconstructed from the corrected first and second projection datasets. In this way, metal artifacts may be substantially reduced in dual or multi-energy CT imaging.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 6:
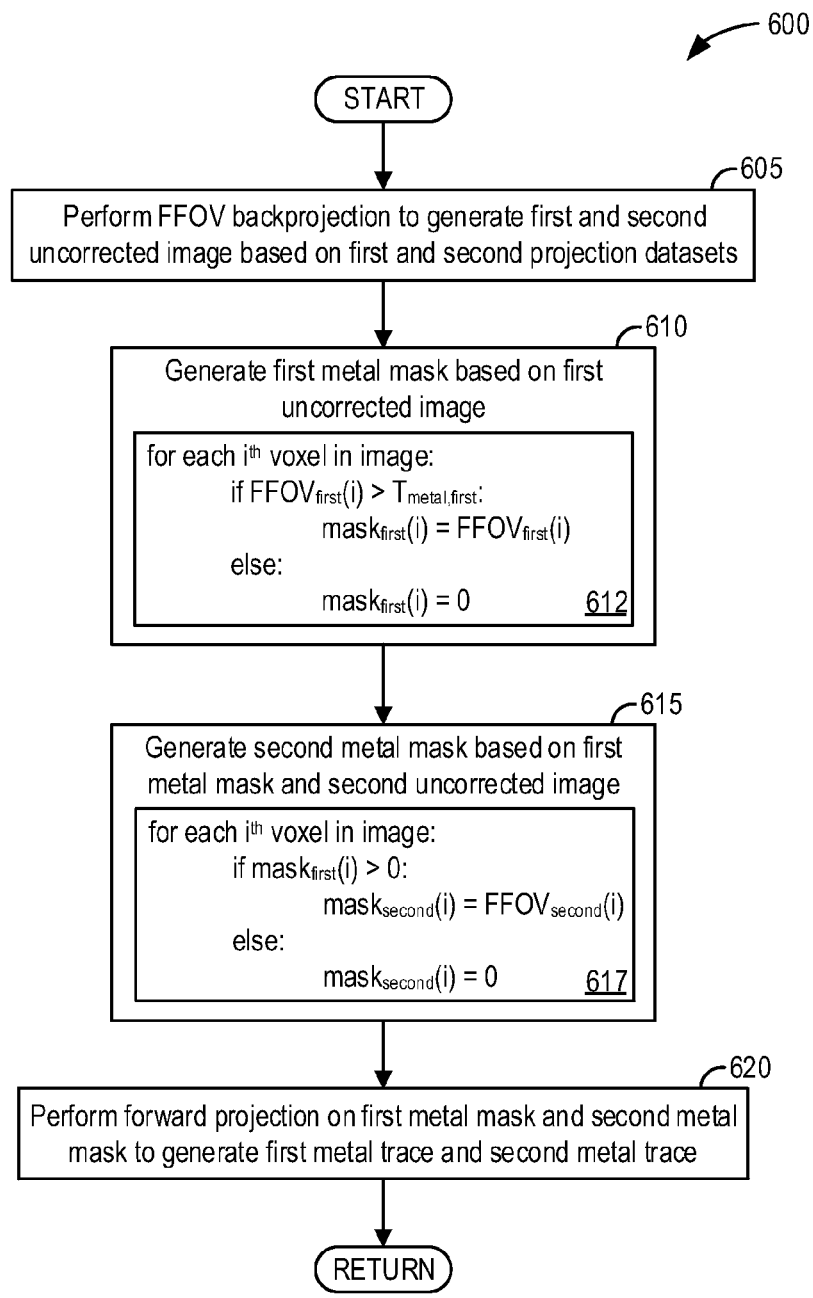
FIG. 6 is a high-level flow chart illustrating an example method for guided metal mask generation according to an embodiment of the invention.
Figure 7:
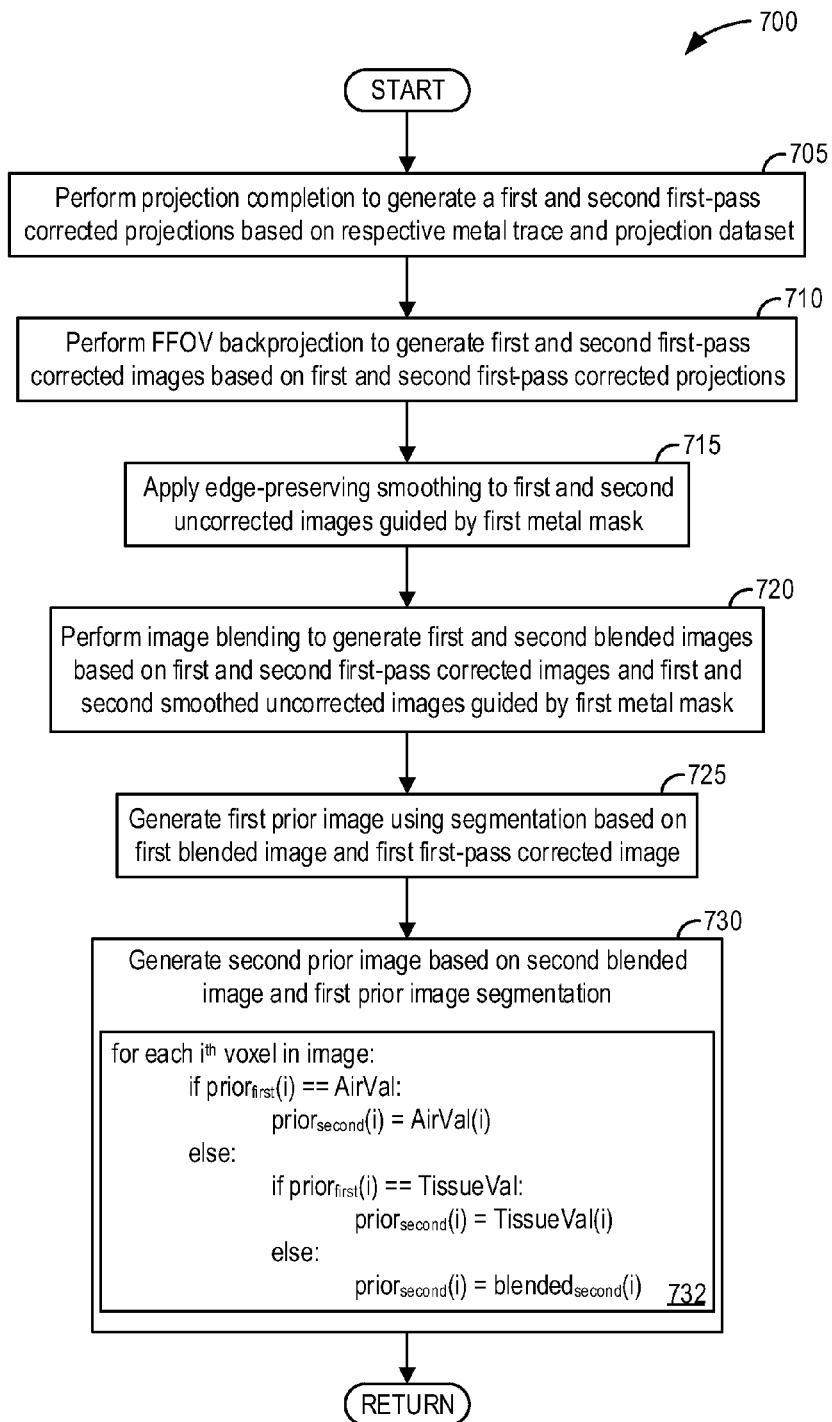
FIG. 7 is a high-level flow chart illustrating an example method for guided prior image generation according to an embodiment of the invention.
Figure 8:
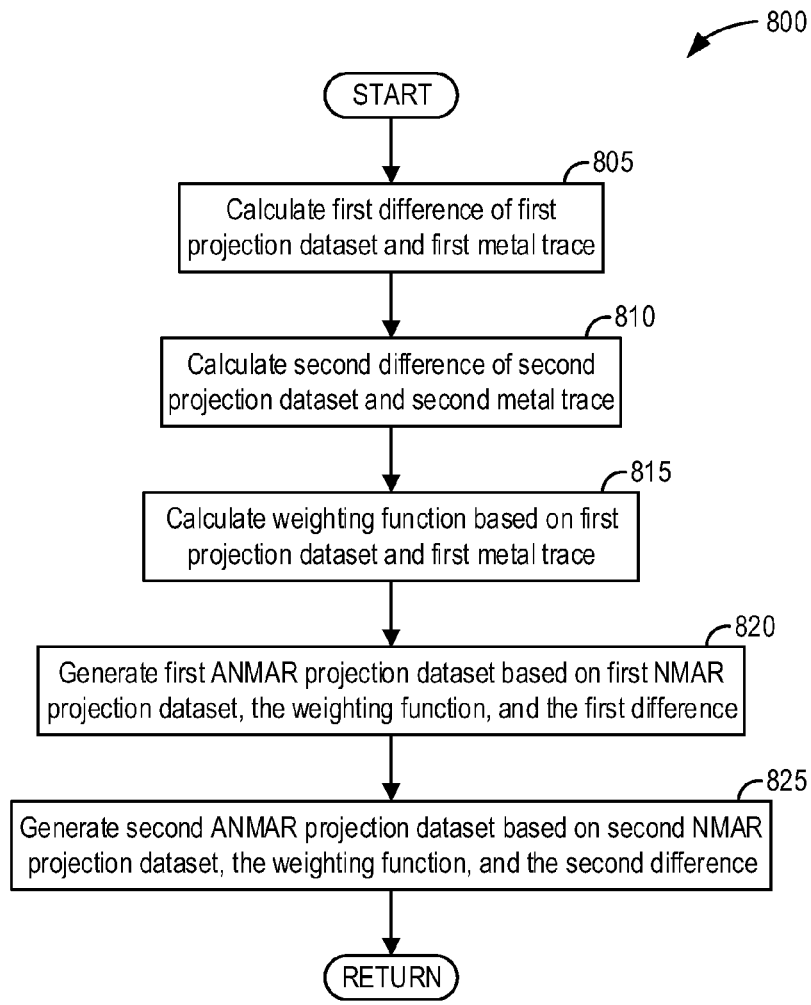
FIG. 8 is a high-level flow chart illustrating an example method for guided adaptive normalized metal artifact reduction according to an embodiment of the invention.
Figure 9:
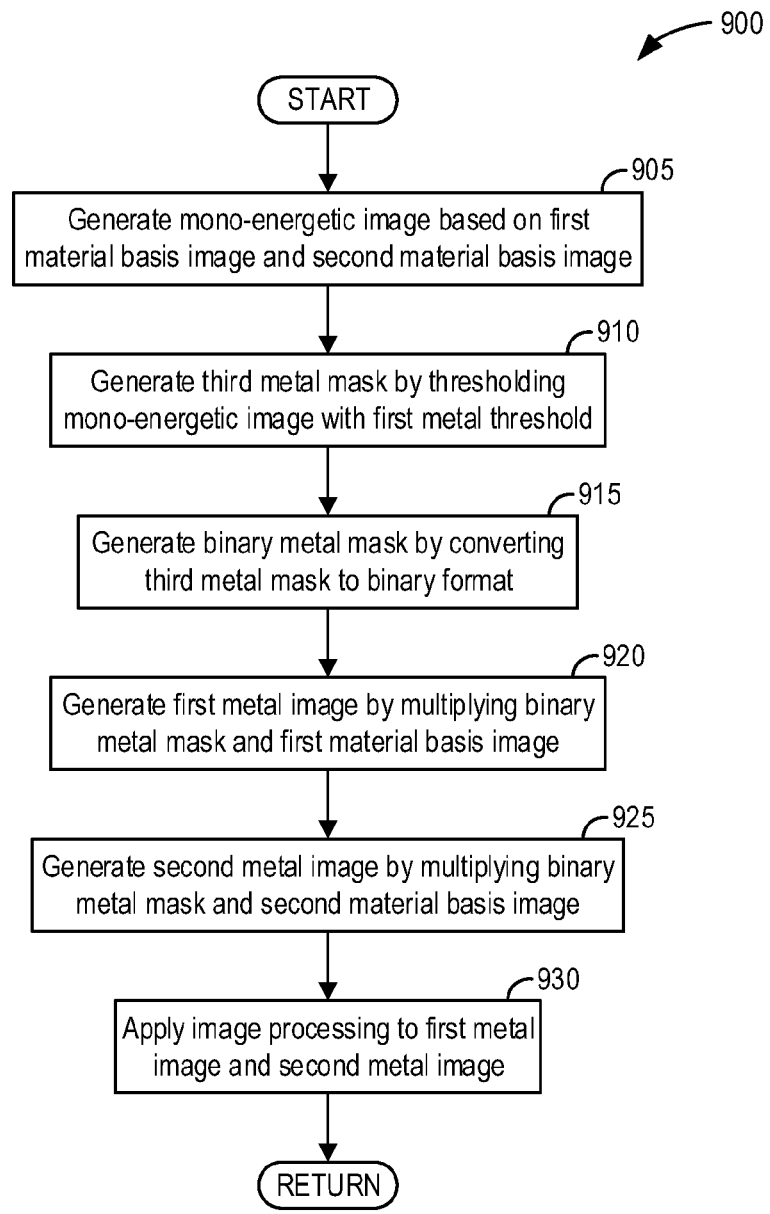
FIG. 9 is a high-level flow chart illustrating an example method for guided metal image generation according to an embodiment of the invention.

The following description relates to various embodiments of image reconstruction for dual energy spectral imaging. In particular, methods and systems for metal artifact reduction are disclosed. The operating environment of the present invention is described with respect to a sixty-four-slice computed tomography (CT) system, such as the CT imaging system shown in FIGS. 1-4. As described herein above, the presence of metal in an object being imaged (e.g., a patient, packages, etc.) may interfere with x-ray attenuation during CT imaging, thereby leading to metal artifacts in reconstructed images of the object. In dual or multi-energy CT imaging, multiple projection datasets may be acquired, where each projection dataset corresponds to a different acquisition energy. A method for dual or multi-energy imaging, such as the method depicted in FIG. 5, may include applying a metal artifact reduction algorithm to the multiple projection datasets, where the application of the metal artifact reduction algorithm to one of the multiple projection datasets is used to guide the application of the metal artifact reduction algorithm to the other projection datasets. In particular, since the attenuation of x-rays through metal is greater at lower energies than at higher energies, the projection dataset acquired at the highest energy may be used to guide metal artifact reduction in the lower energy projection datasets. The metal artifact reduction algorithm may include performing guided metal mask generation, as depicted in FIG. 6. The metal artifact reduction algorithm may further include performing guided prior image generation, as depicted in FIG. 7. Even further, the metal artifact reduction algorithm may include performing guided adaptive normalized metal artifact reduction, as depicted in FIG. 8. The metal artifact reduction algorithm generates an estimate of what the image would look like if no metal were present. However, since physicians may be confused by the absence of the metal in the final reconstructed image, images containing only the metal may be generated, as depicted in FIG. 9, so that the metal can be added back to the corrected images to provide an accurate image free of metal artifacts. Finally, the metal artifact reduction algorithm may be utilized for luggage/package inspection systems, such as the system depicted in FIG. 10.

Though a sixty-four-slice CT system is described by way of example, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic radiation. The invention will be described with respect to a "third generation" CT scanner, but is equally applicable with other CT systems as well as vascular and surgical C-arm systems and other x-ray tomography systems.

As used herein, the term "metal" is used to denote objects or voxels in the image corresponding to high x-ray attenuation properties even if those objects are not metal.

Figure 1:
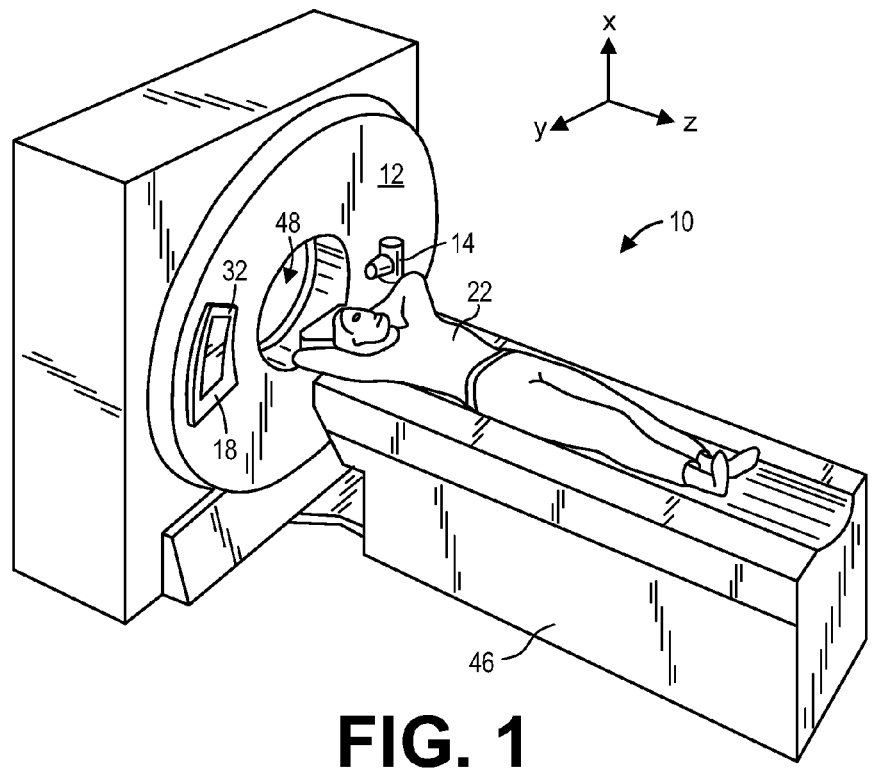
FIG. 1 is a pictorial view of an imaging system according to an embodiment of the invention.
Figure 2:
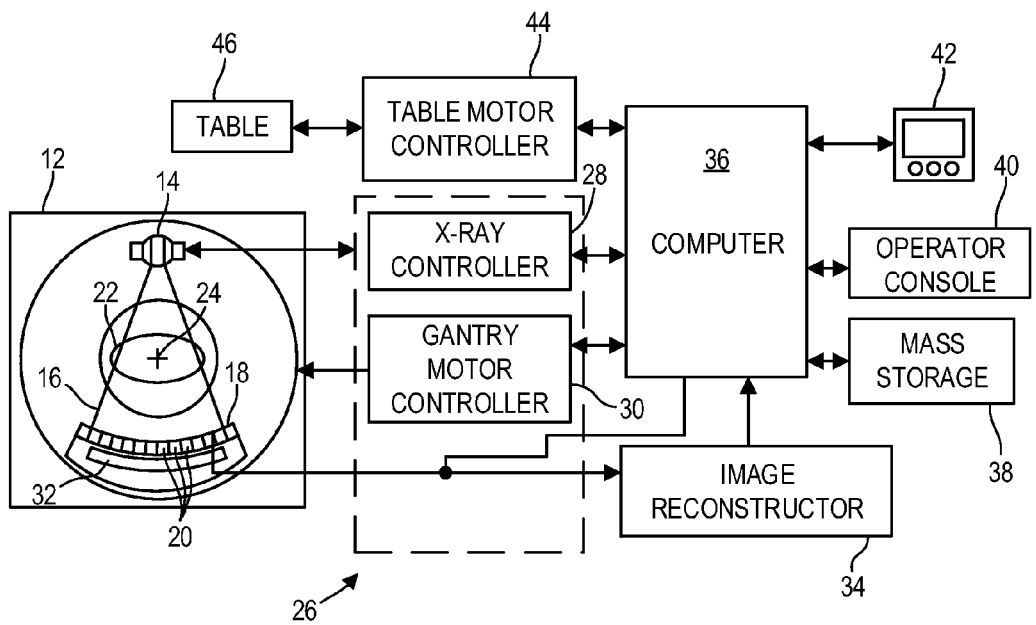
FIG. 2 is a block schematic diagram of an exemplary imaging system according to an embodiment of the invention.

Referring to FIGS. 1 and 2, a CT imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. Detector assembly 18 is formed by a plurality of detectors 20 and data acquisition system (DAS) 32. The plurality of detectors 20 sense the projected x-rays that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44 which controls a motorized table 46 to position patient 22 and gantry 12. Particularly, table 46 moves patient 22 through a gantry opening 48 of FIG. 1 in whole or in part.

Figure 3:
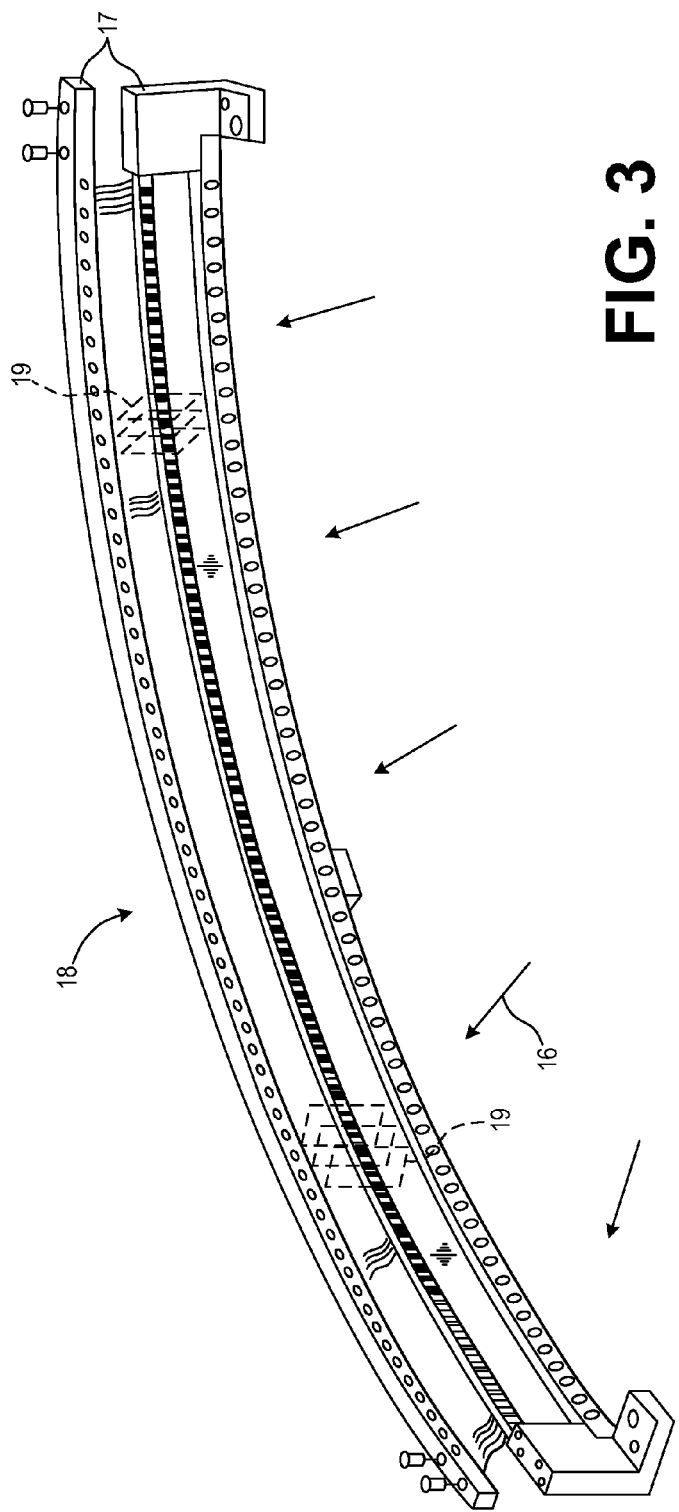
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12.

Figure 4:
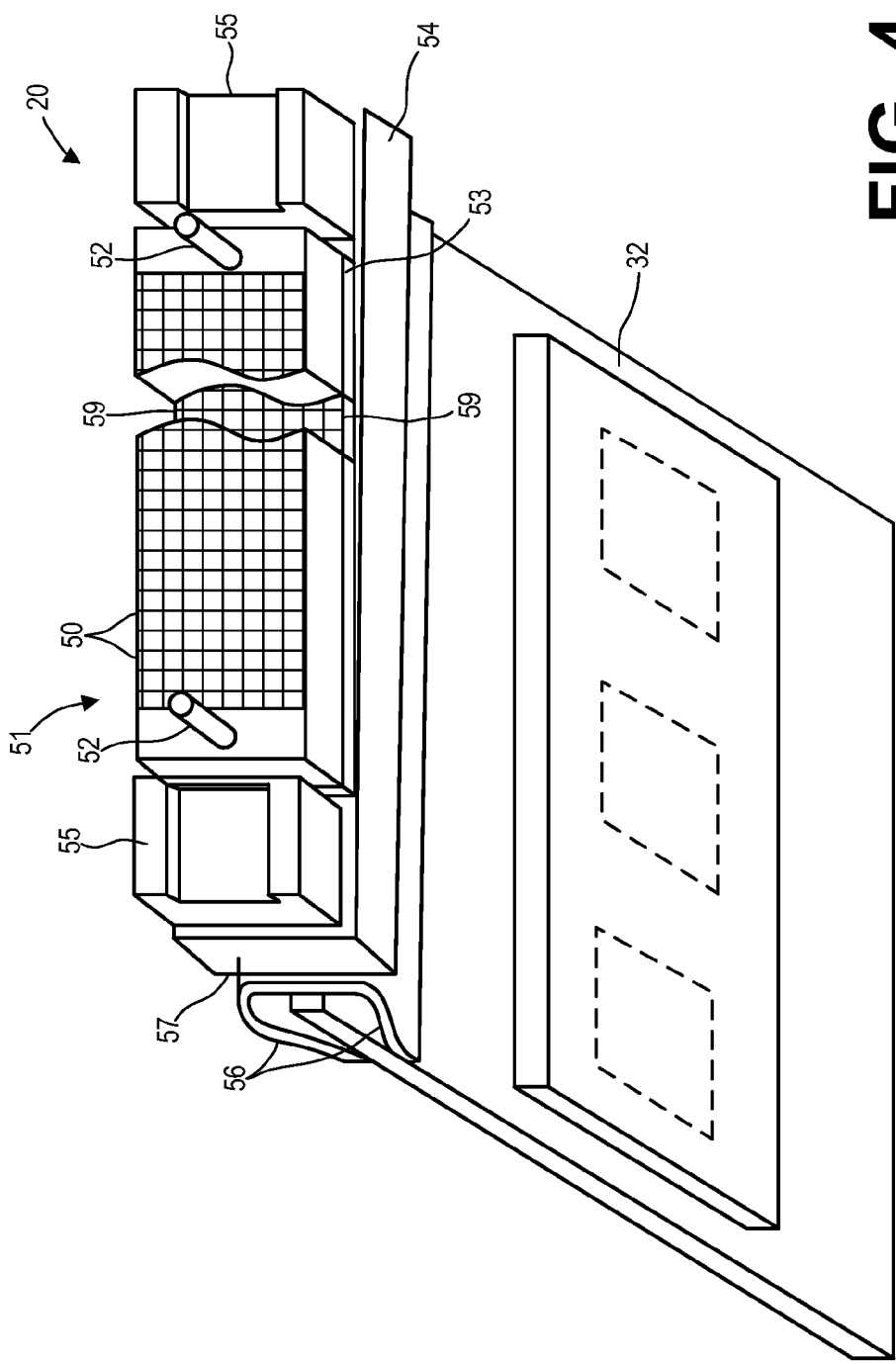
FIG. 4 is a perspective view of one embodiment of a CT detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

As described above, each detector 20 may be designed to directly convert radiographic energy to electrical signals containing energy discriminatory or photon count data. Thus, in an alternate preferred embodiment, each detector 20 includes a semiconductor layer fabricated from CZT. Each detector 20 also includes a plurality of metallized anodes attached to the semiconductor layer. Such detectors 20 may include an electrical circuit having multiple comparators thereon which may reduce statistical error due to pileup of multiple energy events.

Referring back to FIGS. 1 and 2, a discussion is now presented in connection with a decomposition algorithm. An image or slice is computed which may incorporate, in certain modes, less or more than 360 degrees of projection data to formulate an image. The image may be collimated to desired dimensions using tungsten blades in front of the x-ray source and different detector apertures. A collimator typically defines the size and shape of the beam of x-rays 16 that emerges from the x-ray source 14, and a bowtie filter may be included in the system 10 to further control the dose to the patient 22. A typical bowtie filter attenuates the beam of x-rays 16 to accommodate the body part being imaged, such as head or torso, such that, in general, less attenuation is provided for x-rays passing through or near an isocenter of the patient 22. The bowtie filter shapes the x-ray intensity during imaging in accordance with the region-of-interest (ROI), field of view (FOV), and/or target region of the patient 22 being imaged.

As the x-ray source 14 and the detector array 18 rotate, the detector array 18 collects data of the attenuated x-ray beams. The data collected by the detector array 18 undergoes pre-processing and calibration to condition the data to represent the line integrals of the attenuation coefficients of the scanned object or the patient 22. The processed data are commonly called projections.

In dual or multi-energy imaging, two or more sets of projection data are typically obtained for the imaged object at different tube peak kilovoltage (kVp) levels, which change the peak and spectrum of energy of the incident photons comprising the emitted x-ray beams or, alternatively, at a single tube peak kilovoltage (kVp) level or spectrum with an energy resolving detector of the detector array 18. Regarding terminology, a set of projection data obtained at a higher tube kVp level may be interchangeably referred to herein as a high kVp dataset or a high energy dataset, while a set of projection data obtained at a lower tube kVp level may be interchangeably referred to herein as a low kVp dataset or a low energy dataset.

The acquired sets of projection data may be used for basis material decomposition (BMD). During BMD, the measured projections are converted to a set of density line-integral projections. The density line-integral projections may be reconstructed to form a density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the CT system 10 reveals internal features of the patient 22, expressed in the densities of the two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In addition to a CT number or Hounsfield value, an energy selective CT system can provide additional information related to a material's atomic number and density. This information may be particularly useful for a number of medical clinical applications, where the CT number of different materials may be similar but the atomic number may be quite different. For example, calcified plaque and iodine-contrast enhanced blood may be located together in coronary arteries or other vessels. As will be appreciated by those skilled in the art, calcified plaque and iodine-contrast enhanced blood are known have distinctly different atomic numbers, but at certain densities these two materials are indistinguishable by CT number alone.

A decomposition algorithm is employable to generate atomic number and density information from energy sensitive x-ray measurements. Multiple energy techniques comprise dual energy, photon counting energy discrimination, dual layered scintillation and/or one or more other techniques designed to measure x-ray attenuation in two or more distinct energy ranges. As an example, a compound or mixture of materials measured with a multiple energy technique may be represented as a hypothetical material having the same x-ray energy attenuation characteristics. This hypothetical material can be assigned an effective atomic number Z. Unlike the atomic number of an element, effective atomic number of a compound is defined by the x-ray attenuation characteristics, and it needs not be an integer. This effective Z representation property stems from a well-known fact that x-ray attenuation in the energy range useful for diagnostic x-ray imaging is strongly related to the electron density of compounds, which is also related to the atomic number of materials.

The basis for the present disclosure is the fact that high energy photons penetrate metal more easily than low energy photons. As a result, high energy projection datasets include fewer metal artifacts in comparison to low energy projection datasets. For this reason, the location of metal may be more accurately determined in the high energy projection datasets, since there are fewer metal artifacts obscuring the location of metal. As described further herein, a method for metal artifact reduction in spectral CT imaging may comprise applying metal artifact reduction to each projection dataset, where the application of metal artifact reduction to the highest energy projection dataset is used to guide the application of metal artifact reduction to the lower energy projection datasets. In this way, metal artifact reduction may be consistently applied to a plurality of projection datasets, thereby reducing (or substantially eliminating) the generation of new artifacts during material decomposition in dual or multi-energy CT imaging.

Figure 5:
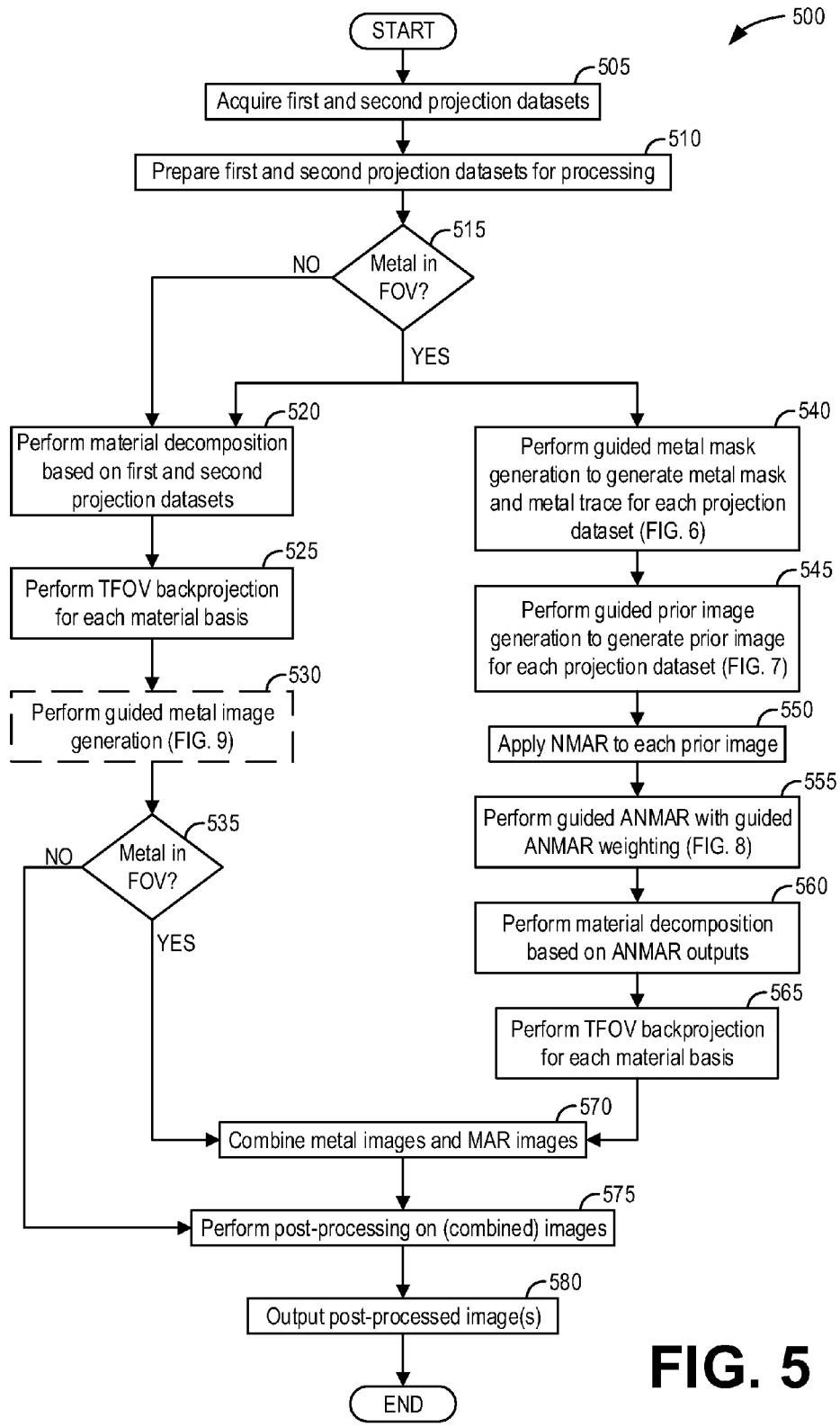
FIG. 5 is a high-level flow chart illustrating an example method for metal artifact reduction according to an embodiment of the invention.

FIG. 5 is a high-level flow chart illustrating an example method 500 for metal artifact reduction according to an embodiment of the invention. In particular, method 500 relates to guided metal artifact reduction for spectral (i.e., dual or multi-energy) imaging, wherein metal artifact reduction applied to a first projection dataset is used to guide metal artifact reduction applied to a second projection dataset. As described further herein, the first projection dataset may correspond to a high energy projection dataset while the second projection dataset may correspond to a low energy projection dataset. Method 500 may be described with reference to the system and components shown in FIGS. 1-4, however the method may be applied to other systems without departing from the scope of the present disclosure.

Method 500 may begin at 505. At 305, method 300 may include acquiring a first projection dataset and a second projection dataset. For example, the first projection dataset may comprise a high energy projection dataset and the second projection dataset may comprise a low energy projection dataset. The first and second projection datasets may be acquired using any dual or multi-energy CT imaging technology, including but not limited to fast kV switching, two-tube two-detector (2T2D), dual layer, rotate-rotate, photon counting, and so on. After acquiring the datasets, method 500 may continue to 510.

At 510, method 500 may include preparing the first and second projection datasets for processing. Preparing the first and second projection datasets for processing may include, as non-limiting examples, time-aligning views between the first and second projection datasets, interpolating missing data, applying gain normalization, applying data corrections for detector artifacts, and so on. After preparing the datasets for processing, method 500 may continue to 515.

At 515, method 500 may include determining if metal is present in the field of view (FOV). For example, a metal implant may be located within the patient 22 and within the FOV scanned by the imaging system 10. In such an example, the metal may reflect or otherwise interfere with the transmission of x-rays 16 through the metal, thereby introducing metal artifacts in images reconstructed from the acquired projections. In one example, determining if metal is present in the FOV may comprise determining if an operator has indicated, via the operator console 40, that metal is present within the FOV. Additionally or alternatively, determining if metal is present in the FOV may comprise detecting metal within the body. Such metal detection may be carried out prior to the acquisition scan, for example during a scout scan or prior to the patient 22 laying on the table 46. As described further herein, metal artifact reduction (MAR) may be applied to the acquired projection data to substantially reduce metal artifacts in images reconstructed from the acquired projection data. Determining if metal is present in the FOV therefore determines whether or not the method 500 will apply MAR to the acquired projection data.

In some examples, the FOV may comprise the target field of view (TFOV). For example, in cardiac imaging, a high-resolution image of a small sub-region of the patient's anatomy may be desired. In such an example, if the entire patient is scanned, the full field of view (FFOV) comprises the all acquired projection data, while the TFOV may only comprise a subset of the acquired projection data, for example the subset may include the heart of the patient. If metal is present in the FFOV but not in the TFOV, for example if the patient has a metal implant in his or her leg but the TFOV is centered on the patient's heart, metal artifacts may not occur in the TFOV despite the presence of metal in the FFOV. In such examples, determining if metal is present in the FOV may comprise determining if metal is present in the TFOV. However, in some examples the FOV may comprise the FFOV. For example, if the patient has a metal implant in his or her torso but the TFOV is centered on the heart, metal artifacts may occur in the TFOV even if the metal is present outside of the TFOV. In such examples, determining if metal is present in the FOV may comprise determining if metal is present in the FFOV. In yet other examples, determining if metal is present in the FOV may comprise determining if metal is present in the FFOV, regardless of the proximity of the metal to the TFOV.

If metal is present in the FOV, method 500 may continue to both 520 and 540. Note that method 500 includes two branches performed in parallel. Steps 520 through 530 comprise a non-MAR branch wherein metal images are generated and no metal artifact reduction is performed, while steps 540 through 565 comprise a MAR branch wherein MAR images are generated and metal artifact reduction is performed.

At 540, method 500 may include performing guided metal mask generation to generate a metal mask and a metal trace for each projection dataset. A metal mask comprises a projection dataset comprising views including metal, while a metal trace comprises an image dataset comprising views including metal. As described further herein, the metal trace may be generated by backprojecting the metal mask. Generating a metal mask may comprise performing simple thresholding on a (processed) projection dataset, such as a projection dataset acquired at 505 and processed at 510. For example, for dual energy imaging wherein a higher energy projection dataset and a lower energy projection dataset are acquired, a first metal mask may be generated by applying simple thresholding to the higher energy projection dataset with a first metal threshold. A second metal mask may then be generated based on the first metal mask and the lower energy projection dataset. In particular, the second metal mask may select values in the lower energy projection dataset corresponding to the positions of the first metal mask. A method for performing guided metal mask generation is described further herein with regard to FIG. 6.

At 545, method 500 may include performing guided prior image generation to generate a prior image for each projection dataset. Performing guided prior image generation may comprise generating a first prior image based on the first projection dataset, and then generating a second prior image based on the second projection dataset and the first prior image. A method for performing guided prior image generation is described further herein and with regard to FIG. 7.

At 550, method 500 may include applying normalized metal artifact reduction (NMAR) to each prior image. NMAR comprises a method for replacing corrupted sinogram samples in an original projection dataset. For example, the first projection dataset is normalized by a forward projection of the first prior image to create a first normalized projection dataset. Then, the corrupted samples in the first projection dataset are replaced (or inpainted) using linear interpolation on the first normalized projection dataset. The location of the corrupted samples in the first projection dataset may be determined using the first metal trace. Finally, the linearly-interpolated projection dataset is then de-normalized with the forward projection of the first prior image. The first de-normalized projection dataset, hereinafter referred to as the first NMAR projection dataset, comprises values from the forward-projected first prior image in the region corrupted by metal.

The second projection dataset is similarly normalized by a forward projection of the second prior image, corrupted samples in the normalized projection dataset are inpainted using linear interpolation in the regions of the second normalized projection dataset indicated by the second metal mask, and the linearly-interpolated projection dataset is then de-normalized with the forward projection of the second prior image, thereby creating a second NMAR projection dataset.

In some examples, the metal trace may be subtracted from the projection dataset to create a metal-free projection dataset (i.e., a projection dataset with metal-filled regions removed rather than replaced), and NMAR may be applied to the metal-free projection dataset rather than the projection dataset itself. The NMAR projection datasets comprise an approximation of what the original projection datasets would look like if metal were not present in the patient, and feature a high resolution since the NMAR projection datasets are based on the original projection datasets, which have the highest resolution possible. However, resolution of the projections near the metal may be degraded due to the interpolation, so after applying NMAR method 500 may proceed to 555.

At 555, method 500 may include performing guided adaptive NMAR (ANMAR) with guided ANMAR weighting to generate ANMAR projection datasets. ANMAR may be utilized to improve resolution in the vicinity of metal. ANMAR comprises blending the NMAR projection datasets with the difference of original views (i.e., projection datasets) and the metal trace using a weighting function. The weighting function may be generated based on the first NMAR projection dataset and the first difference between the first projection dataset and the first metal trace, and may be used to perform ANMAR for both the first NMAR projection dataset and the second NMAR projection dataset. In this way, the application of ANMAR in the second channel (specifically, to the second NMAR projection dataset) may be guided by the application of ANMAR in the first channel (specifically, to the first NMAR projection dataset). A method for performing guided ANMAR is described further herein with regard to FIG. 8.

After performing ANMAR to generate the first and second ANMAR projection datasets, the metal artifact reduction algorithm is complete. That is, the ANMAR projection datasets comprise fully-corrected (with respect to metal artifacts) metal-free projection datasets.

At 560, method 500 may include performing material decomposition based on the ANMAR projection datasets. Performing material decomposition comprises decomposing the ANMAR projection datasets into a first material basis and a second material basis. Decomposition may be performed using, for example, basis material decomposition (BMD) wherein the projections are converted to a set of density line-integral projections as described herein above and known in the art. The material bases may comprise, for example, a water basis and an iodine basis. In other examples, the material bases may comprise different combinations of materials.

At 565, method 500 may include performing TFOV backprojection for each material basis to generate MAR material basis images. Performing TFOV backprojection may comprise applying an analytic reconstruction technique, such as filtered back projection (FBP), to the TFOV.

Thus method 500 includes the generation of MAR images, which approximate what an uncorrected image would look like if no metal were present. In other words, the MAR images are, at least for the most part, free of metal and metal artifacts. However, since the metal is present, an end user (e.g., an imaging operator, a physician, a patient, etc.) expects to see the metal when reviewing the final image. As described further herein, metal images may be generated and superimposed over the MAR images to create accurate images of the scanned volume without metal artifacts.

Returning to 515, recall that if metal is present, method 500 also proceeds to 520. At 520, method 500 may include performing material decomposition (MD) based on the first and second projection datasets. Performing MD comprises decomposing the first and second projection datasets into a first non-MAR material basis and a second non-MAR material basis. Decomposition may be performed using, for example, BMD as described above. The material bases may comprise, for example, a water basis and an iodine basis. In other examples, the material bases may comprise different combinations of materials.

After performing MD, method 500 may continue to 525. At 525, method 500 may include performing TFOV backprojection for each material basis. For example, FBP may be applied to the first non-MAR material basis and the second non-MAR material basis to generate, respectively, a first non-MAR material basis image and a second non-MAR material basis image. Note that the first non-MAR material basis image and the second non-MAR material basis image may not directly correspond to the first projection dataset and the second projection dataset, but instead each non-MAR material basis image may be based on a combination of the first projection dataset and the second projection dataset.

After generating the non-MAR material basis images, method 500 may continue to 530. At 530, method 500 may include performing guided metal image generation. A method for performing guided metal image generation is described further herein with regard to FIG. 9. The method may include, as a non-limiting example, generating a mono-energetic image based on the first non-MAR material basis image and the second non-MAR material basis image. The method may further include generating a third metal mask by thresholding the mono-energetic image with the first metal threshold, where the first metal threshold is the same metal threshold used to generate the first metal mask at 540. The method may further include generating a binary metal mask by converting the third metal mask to a binary format. After generating the binary metal mask, the method may further include generating a first metal image by multiplying the binary metal mask and the first non-MAR material basis image, and generating a second metal image by multiplying the binary metal mask and the second non-MAR material basis image. The first and second metal images thus comprise only the metal portions of the first and second non-MAR material basis images.

At 535, method 500 may include determining if metal is present in the FOV. Since metal was already determined to be present at 515, method 500 may continue to 570.

At 570, method 500 may include combining metal images and MAR images. In particular, the first and second metal images generated at 530 may be combined respectively with the first and second MAR images generated at 565. In this way, the combined images may include the metal present in the FOV, as expected by the imaging system operator and/or physician, but without metal artifacts arising from the metal. Further, since the metal artifact reduction on each channel (i.e., the first and the second channel, or the high and the low energy channel) is synchronized, no additional artifacts are introduced during material decomposition.

At 575, method 500 may include performing post-processing on the combined images. Post-processing may include any additional artifact reduction algorithms, alignment, stitching, and so on. In examples where metal is not present in the FOV, post-processing may include generating a mono-energetic image based on the non-MAR material basis images. Generating a mono-energetic image may comprise, as an example, generating a weighted sum of the non-MAR material basis images. In examples where metal is present in the FOV, post-processing may include generating a mono-energetic image based on the combined images (i.e., the images comprising a combination of metal and MAR images). Generating a mono-energetic image may comprise generating a weighted sum of the combined images.

Finally, at 580, method 500 may include outputting the post-processed images. Outputting the post-processed images may comprise outputting the images to a display, such as display 42, for review by an imaging system operator and/or a physician. Outputting the post-processed images may also comprise outputting the images to non-transitory memory, such as mass storage 38, for subsequent retrieval and review. Method 500 may then end.

Returning to 515, if no metal is present, method 500 may continue to 520. At 520, method 500 may include performing material decomposition (MD) based on the first and second projection datasets. As described above, performing MD comprises decomposing, via BMD for example, the first and second projection datasets into a first material basis and a second material basis.

Continuing at 525, method 500 may include performing TFOV backprojection for each material basis to generate a first material basis image and a second material basis image.

At 530, method 500 may optionally include performing guided metal image generation. However, since no metal is present in the FOV, there is no reason to perform guided metal image generation and therefore action 530 may not be performed.

At 535, method 500 may include determining if metal is present in the FOV. Since no metal is present, method 500 may continue to 575. At 575, method 500 may include performing post-processing on the material basis images. As described above, post-processing may include performing any additional artifact reduction algorithms, alignment, stitching, and so on. In some examples, post-processing may include generating a mono-energetic image based on the material basis images.

Finally, at 580, method 500 may include outputting the post-processed image. Outputting the post-processed images may comprise outputting the images to a display, such as display 42, for review by an imaging system operator and/or a physician. Outputting the post-processed images may also comprise outputting the images to non-transitory memory, such as mass storage 38, for subsequent retrieval and review. Method 500 may then end. In this way, metal artifact reduction may not be applied to the projection datasets when no metal is present in the FOV.

Thus, a method for metal artifact reduction in dual or multi-energy spectral computed tomography imaging is provided. The method may include guiding an application of metal artifact reduction to a lower energy projection dataset based on an application of metal artifact reduction to a higher energy projection dataset, so that the metal artifact reduction may be consistently applied in each channel. While a general and high-level description of guided metal artifact reduction is described herein above with regard to FIG. 5, several subroutines for guided metal artifact reduction are further described herein with respect to FIGS. 6 through 9.

FIG. 6 is a high-level flow chart illustrating an example method 600 for guided metal mask generation according to an embodiment of the invention. In particular, method 600 relates to generating a first metal mask for a first projection dataset, and using the first metal mask to guide the generation of a second metal mask for a second projection dataset. Method 600 may comprise a subroutine of the method 500 depicted in FIG. 5. In particular, method 600 may comprise the action 540 of method 500. Method 600 may be described with reference to the system and components shown in FIGS. 1-4, however the method may be applied to other systems without departing from the scope of the present disclosure.

Method 600 begins at 605. At 605, method 600 may include performing full field of view (FFOV) backprojection to generate a first and a second uncorrected image based on the first and second projection datasets.

At 610, method 600 may include generating a first metal mask based on the first uncorrected image. Generating the first metal mask may comprise segmenting the first uncorrected image using a threshold value to indicate metal voxels within the first uncorrected image. The segmentation generates the first metal mask by applying a metal threshold to the first uncorrected image and inserting any voxels above the metal threshold value into the first metal mask. The metal threshold may comprise a first metal threshold, where the first metal threshold comprises a metal threshold applicable to the first projection dataset. Pseudocode for generating the first metal mask is depicted at 612. For each $i^{th}$ voxel in the first uncorrected image (FFOV$_{first}$), if the value of the first uncorrected image at a given voxel is greater than the first metal threshold (i.e., if FFOV$_{first}$(i)>T$_{metal,first}$), then the first metal mask at that voxel is set to the value of the first uncorrected image at that voxel (i.e., mask$_{first}$(i)= FFOV$_{first}$(i)). Otherwise, for example if the value of the first uncorrected image at that voxel is less than the first metal threshold, then the value of the first metal mask at that voxel is set to zero (i.e., mask$_{first}$(i)=0).

After generating the first metal mask, method 600 may continue to 615. At 615, method 600 may include generating a second metal mask based on the first metal mask and the second uncorrected image. Pseudocode for generating the second metal mask is depicted at 617. For each $i^{th}$ voxel in the image, if the first metal mask has a non-zero value (i.e., if mask$_{first}$(i)>0), then the second metal mask at that voxel is set to the value of the second uncorrected image at that voxel (i.e., mask$_{second}$(i)=FFOV$_{second}$(i)). Otherwise, for example if the first metal mask has a zero value, then the second metal mask at that voxel is set to zero (i.e., mask$_{second}$(i)=0). In this way, the generation of the second metal mask is guided by the first metal mask. That is, the location of the metal mask in both the first and the second channels are the same although the values in each may differ.

At 620, method 600 may include performing a forward projection on the first metal mask and the second metal mask to respectively generate a first metal trace and a second metal trace. Specifically, the metal voxels, which may be indicated by non-zero values in the metal masks, are projected onto the detector for a given source position. Those detector pixels or dexels that have a non-zero contribution from the forward projection are labeled as metal detector pixels or metal dexels. Method 600 may then return.

FIG. 7 is a high-level flow chart illustrating an example method 700 for guided prior image generation according to an embodiment of the invention. In particular, method 700 relates to generating a first prior image, and using the first prior image to guide the generation of a second prior image. Method 700 may comprise a subroutine of the method 500 depicted in FIG. 5. For example, method 700 may comprise the action 545 of the method 500. Method 700 may be described with reference to the system and components shown in FIGS. 1-4 and the method shown in FIG. 5, however the method may be applied to other systems and methods without departing from the scope of the present disclosure.

Method 700 may begin at 705. At 705, method 700 may include performing projection completion to generate a first and a second first-pass corrected projections based on respective metal traces and projection datasets. Projection completion comprises the removal of metal from the projection dataset using the metal trace. In some examples, projection completion may comprise an interpolation in the original projection dataset at the location of the metal trace.

After projection completion, method 700 may continue to 710. At 710, method 700 may include performing FFOV backprojections to generate a first and a second first-pass corrected images based on the first and second first-pass corrected projections.

At 715, method 700 may include applying edge-preserving smoothing to the first and second uncorrected images guided by the first metal mask. For example, a Gaussian may be applied to the uncorrected images.

At 720, method 700 may include performing image blending to generate first and second blended images based on the first and second first-pass corrected images and the first and second smoothed uncorrected images guided by the first metal mask. In one example, the first-pass corrected images and the smoothed uncorrected images may be combined in the image domain. For example, the first first-pass corrected image and the first smoothed uncorrected image may be separately passed through one or more banks of filters. The filtered first first-pass corrected image may then be combined with the filtered first smoothed uncorrected image using weights generated based on the first metal mask. Specifically, these weights may be spatially varying as a function of the distance from the metal, where the distance from the metal is based on the first metal mask. The second first-pass corrected image and the second smoothed uncorrected image may be similarly filtered and combined using the same weights generated based on the first metal mask. The multi-band filtering and the blending of the first-pass corrected images and the smoothed uncorrected images may be carried out in frequency space. To that end, in some examples, performing image blending may include transforming the images to the frequency space, applying the multi-band filtering and the weighted combination, and then transforming the frequency-space images back to the image domain.

At 725, method 700 may include generating a first prior image using segmentation based on the first blended image and the first first-pass corrected image. First, simple thresholding may be applied to segment air and soft tissue in the first blended image. It should be appreciated that the use of air and soft tissue is exemplary, and in some examples, the first blended image may be segmented based on materials other than air and soft tissue.

After thresholding the first blended image, additional corrections may be applied to the segmented first blended image in order to generate the first prior image. These additional corrections may also reduce the presence of metal artifacts. For example, the first blended image includes information from the first uncorrected image. In cases where the metal artifacts are very high, such artifacts can propagate through from the uncorrected image and show up in the first blended image and the segmented first blended image. At least some of these artifacts can be removed based on the first first-pass corrected image and a set of selection rules. For example, if a voxel is segmented as air in the first blended image but not in the first first-pass corrected image, this is possibly due to high metal artifacts propagating into the first blended image from the original image (i.e., the first uncorrected image). Hence, in such cases, it is better to trust the segmentation of the first first-pass corrected image. Segmented tissue regions may be similarly compared between the segmented first blended image and the first first-pass corrected image. Furthermore, for all other voxels, the prior image is equal to the segmentation result of the first blended image. In this way, the first prior image may be generated.

At 730, method 700 may include generating a second prior image based on the second blended image and the first prior image segmentation. For example, the segmentation of the first prior image may be applied to the second blended image. In some examples, the segmentation of the first prior image may include the corrections determined based on the first first-pass corrected image, as described herein above. Pseudocode for generating the second prior image is depicted at 732. For each $i^{th}$ voxel in the image, if the first prior image at the voxel includes an air value (i.e., if $prior_{first}(i)=AirVal$), then the second prior image at that voxel is set to the air value at that voxel (i.e., $prior_{second}(i)=AirVal(i)$). Otherwise, if the first prior image at the $i^{th}$ voxel includes a tissue value (i.e., if $prior_{first}(i)==TissueVal$), then the second prior image at that voxel is set to the tissue value at that voxel (i.e., $prior_{second}(i)=TissueVal(i)$). Otherwise, the second prior image at the $i^{th}$ voxel may be set to the second blended image at that voxel (i.e., $prior_{second}(i)=blended_{second}(i)$).

After generating the second prior image, method 700 may then return. Specifically, method 700 may return the first and the second prior images to the method 500 described herein above with regard to FIG. 5.

FIG. 8 is a high-level flow chart illustrating an example method 800 for guided ANMAR according to an embodiment of the invention. Method 800 may comprise a subroutine of method 500. For example, method 800 may comprise the action 555 of the method 500 depicted in FIG. 5. Method 800 may be described with reference to the system and components shown in FIGS. 1-4, however the method may be applied to other systems without departing from the scope of the present disclosure.

Method 800 may begin at 805. At 805, method 800 may include calculating a first difference of the first projection dataset and the first metal trace. The first difference comprises the first projection dataset minus the first metal trace. Continuing at 810, method 800 may include calculating a second difference of the second projection dataset and the second metal trace. The second difference comprises the second projection dataset minus the second metal trace.

At 815, method 800 may include calculating a weighting function based on the first projection dataset and the first metal trace. The weighting function may comprise a piecewise function which selects a synthetic view (e.g., the first NMAR projection dataset) in regions where an x-ray passed purely through metal or purely through non-metal, blends the synthetic view and the original view in transition regions between the purely metal and purely non-metal regions. In this way, the resolution in the vicinity of the metal may be improved. In one example, blending the synthetic views and the original views may comprise combining the views based, for example, on a polynomial function.

In some examples, the weighting function may be calculated based on the first metal trace. For example, an upper threshold and a lower threshold may be determined based on the intensity range of the first metal trace, such that regions in the first metal trace with intensity values above the upper threshold include metal, and regions with intensity values below the lower threshold do not include metal. The weighting function may then blend original views with the synthetic views in regions between the upper threshold and the lower threshold, select the synthetic views in regions above the upper threshold, and select original views in regions below the lower threshold.

In another example, the weighting function may be calculated based on the first difference. In this way, regions containing metal may be identified by the absence of a view in the first difference, transition regions may be identified by reduced views in the first difference compared to the original view, and regions free of metal may be identified by zero difference between the first difference and the original view.

Continuing at 820, method 800 may include generating a first ANMAR projection dataset based on the first NMAR projection dataset, the weighting function, and the first difference. In particular, generating the first ANMAR projection dataset may comprise inputting both the first NMAR projection dataset and the first difference into the weighting function, which outputs the first ANMAR projection dataset. The first ANMAR projection dataset thus comprises the first NMAR projection dataset with an improved resolution in the vicinity of metal regions, where views in the first NMAR projection dataset are blended with views in the first difference.

At 825, method 800 may include generating a second ANMAR projection dataset based on the second NMAR projection dataset, the weighting function, and the second difference. In particular, generating the second ANMAR projection dataset may comprise inputting both the second NMAR projection dataset and the second difference into the weighting function, which outputs the second ANMAR projection dataset. The second ANMAR projection dataset thus comprises the second NMAR projection dataset with an improved resolution in the vicinity of metal regions, where views in the second NMAR projection dataset are blended with views in the second difference. Method 800 may then return.

FIG. 9 is a high-level flow chart illustrating an example method 900 for guided metal image generation according to an embodiment of the invention. Method 900 may comprise a subroutine of method 500. For example, method 900 may comprise the action 530 of the method 500 of FIG. 5. Method 900 may be described with reference to the system and components shown in FIGS. 1-4 as well as the method shown in FIG. 5, however the method may be applied to other systems and may be used in conjunction with other methods without departing from the scope of the present disclosure.

Method 900 may begin at 905. At 905, method 900 may include generating a mono-energetic image based on the first non-MAR material basis image and the second non-MAR material basis image. Generating the mono-energetic image may comprise summing the first non-MAR material basis image and the second non-MAR material basis image.

At 910, method 900 may include generating a third metal mask by thresholding the mono-energetic image with the first metal threshold. In particular, the first metal threshold may comprise the same first metal threshold used to generate the first metal mask at action 540 of FIG. 5.

At 915, method 900 may include generating a binary metal mask by converting the third metal mask to a binary format. For example, the value of all pixels away from the metal in the third metal mask may be set to zero while the value of all pixels including metal may be set to unity.

At 920, method 900 may include generating a first metal image by multiplying the binary mask and the first material basis image. Given the binary format of the binary mask, multiplying the binary mask and the first non-MAR material basis image sets the value of all pixels away from the metal in the non-MAR material basis image to zero, while the value of all pixels including metal in the non-MAR material basis image remain the same since the value of the binary mask at those locations is equal to one. Therefore the first metal image comprises an image that only includes metal.

At 925, method 900 may include generating a second metal image by multiplying the binary mask and the second material basis image. In particular, the binary mask generated at 915 may be multiplied with the second non-MAR material basis image to generate the second metal image as described above at 920.

At 930, method 900 may include applying image processing to the first metal image and the second metal image. For example, image processing operations such as dilation, erosion, smoothing, and so on may be applied to the metal images to create the most realistic appearance. Method 900 may then return.

Although first and second projection datasets are described herein above with regard to FIGS. 5-9, where the first and second projection datasets correspond to a higher energy projection dataset and a lower energy projection dataset, respectively, in some embodiments, more than two projection datasets may be acquired at different energies. It should be appreciated that the methods described herein may be applied to any number of projection datasets (greater than or equal to two). In examples where more than two projection datasets are acquired, the first projection dataset as described herein above may correspond to the highest energy projection dataset, while the actions applied to the second projection dataset as described herein above may be applied to each lower energy projection dataset. In this way, metal artifact reduction applied to the highest energy projection dataset may be used to guide metal artifact reduction applied to the lower energy projection datasets.

Figure 10:
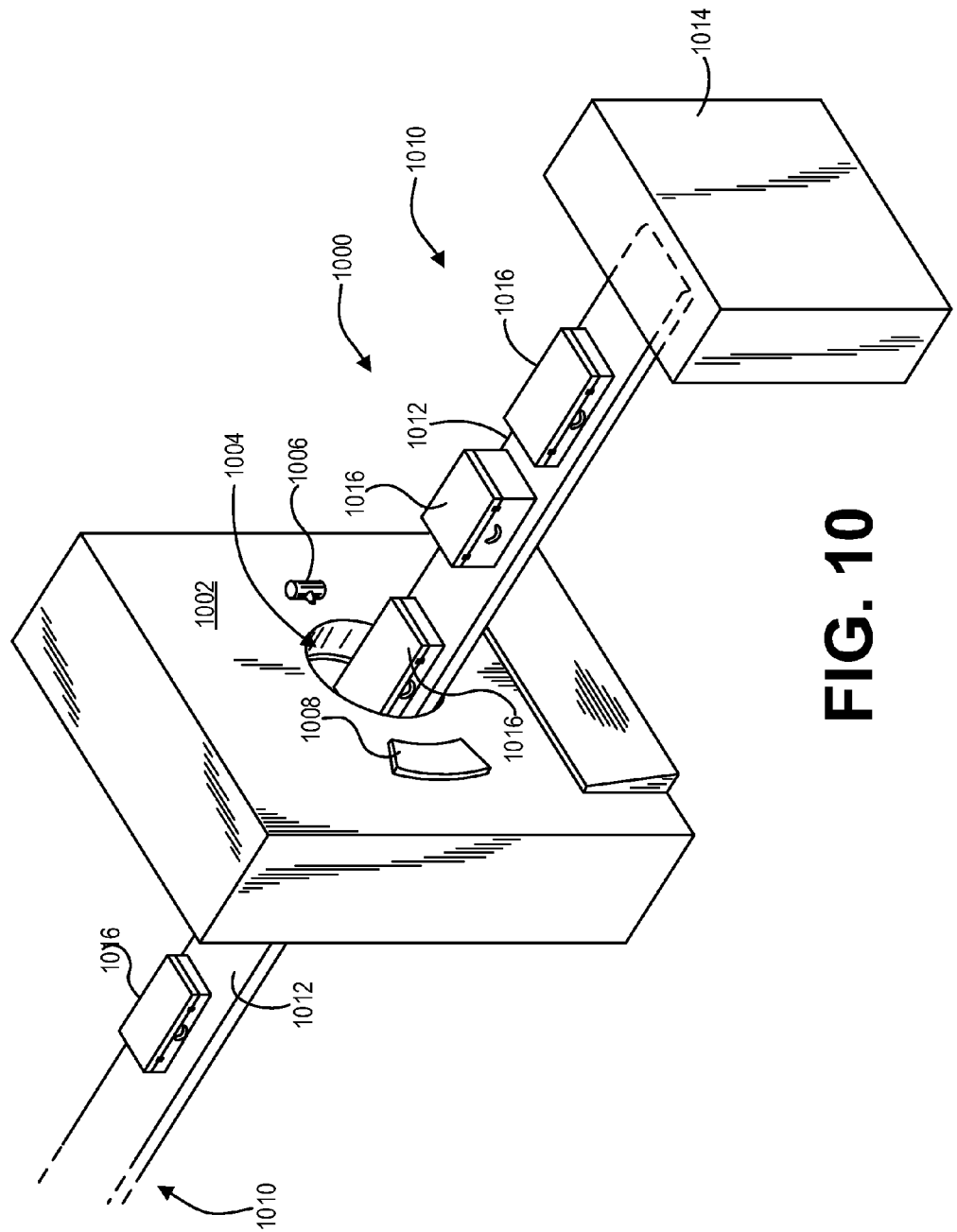
FIG. 10 is a pictorial view of a CT system for use with a non-invasive package inspection system according to an embodiment of the invention.

Referring now to FIG. 10, a package/baggage inspection system 1000 is shown that can use the image acquisition and reconstruction techniques according to embodiments enclosed and which includes a rotatable gantry 1002 having an opening 1004 therein through which packages or pieces of baggage may pass. The rotatable gantry 1002 houses one or more x-ray energy sources 1006 as well as a detector assembly 1008 having scintillator arrays comprising scintillator cells. A conveyor system 1010 is also provided and includes a conveyer belt 1012 supported by structure 1014 to automatically and continuously pass packages or baggage pieces 1016 through opening 1004 to be scanned. Objects 1016 are passed through opening 1004 by conveyor belt 1012, imaging data is then acquired, and the conveyor belt 1012 removes the packages 1016 from opening 1004 in a controlled and continuous manner. As a result, postal inspectors, baggage handlers, and other security personnel may non-invasively inspect the contents of packages 1016 for explosives, knives, guns, contraband, and so on.

An implementation of system 10 and/or 1000 in an example comprises a plurality of components such as one or more of electronic components, hardware components, and/or computer software components. A number of such components can be combined or divided in an implementation of the system 10 and/or 1000. An exemplary component of an implementation of the system 10 and/or 1000 employs and/or comprises a set and/or series of computer instructions written in or implemented with any number of programming languages, as will be appreciated by those skilled in the art. An implementation of system 10 and/or 1000 in an example comprises any (e.g., horizontal, oblique, or vertical) orientation, with the description and figures herein illustrating an exemplary orientation of an implementation of the system 10 and/or 1000, for explanatory purposes.

The technical effect of the disclosure may include the reduction of metal artifacts in reconstructed images. Another technical effect of the disclosure may include the reconstruction of an image from a plurality of projection datasets. Yet another technical effect of the disclosure may include the display of an image reconstructed from a plurality of projection datasets, wherein metal artifacts in the plurality of projection datasets are reduced and wherein one of the plurality of projection datasets is used to guide the reduction of metal artifacts in the other projection datasets. Another technical effect of the disclosure may include the generation of a metal mask for a lower energy projection dataset based on a metal mask generated for a higher energy projection dataset.

In one embodiment, a method comprises acquiring a first projection dataset and a second projection dataset, detecting a location of metal in the first projection dataset, applying corrections to the first and second projection datasets based on the location of the metal, and displaying an image reconstructed from the corrected first and second projection datasets.

In one example, detecting the location of the metal in the first projection dataset comprises generating a first metal mask comprising voxels above a metal threshold in a first backprojection of the first projection dataset. The method further comprises generating a second metal mask comprising voxels in a second backprojection of the second projection dataset at a same location of the voxels in the first metal mask.

As another example, the method further comprises generating a first prior image based on the first projection dataset and the location of the metal, and generating a second prior image based on the second projection dataset and the first prior image.

In another example, the method further comprises segmenting the first prior image into at least two regions based on selected threshold values. In such an example, generating the second prior image based on the first prior image comprises generating the second prior image based on the segmentation of the first prior image.

As another example, generating the second prior image based on the first prior image comprises transforming pixel values of the first prior image based on an acquisition energy of the second projection dataset.

In one example, applying the corrections comprises generating a first interpolated projection dataset based on a forward projection of the first prior image, and generating a second interpolated projection dataset based on a forward projection of the second prior image. In yet another example, applying the corrections further comprises calculating a weighting function based on the first interpolated projection dataset and the location of the metal, blending the first interpolated projection dataset with the first projection dataset based on the weighting function, and blending the second interpolated projection dataset with the second projection dataset based on the weighting function.

In some examples, the method further comprises generating a first metal image and a second metal image based on the metal threshold.

In one example, the first projection dataset comprises a higher energy projection dataset and the second projection dataset comprises a lower energy projection dataset.

In another embodiment, a method comprises: acquiring a first projection dataset and a second projection dataset; generating a first metal-reduced projection dataset based on the first projection dataset and a second metal-reduced projection dataset based on the second projection dataset, wherein generating the second metal-reduced projection dataset is further based on the first projection dataset; decomposing the first and the second metal-reduced projection datasets into a first metal-reduced material basis and a second metal-reduced material basis, and the first and the second projection datasets into a first material basis and a second material basis; reconstructing a first metal-reduced material image based on the first metal-reduced material basis, a second metal-reduced material image based on the second metal-reduced material basis, a first material image based on the first material basis, and a second material image based on the second material basis; generating a first metal image based on the first material image and a second metal image based on the second material image; generating a first metal-corrected image by combining the first metal image and the first metal-reduced material image; generating a second metal-corrected image by combining the second metal image and the second metal-reduced material image; and outputting at least one of the first metal-corrected image, the second metal-corrected image, and a mono-energetic image comprising a combination of the first metal-corrected image and the second metal-corrected image.

In one example, generating the first metal-reduced projection dataset and the second metal-reduced projection dataset comprises: generating a first metal mask based on the first projection dataset, and a second metal mask based on the first metal mask and the second projection dataset; generating a first prior image based on the first projection dataset and the first metal mask, and a second prior image based on the first prior image; interpolating the first projection dataset based on the first metal mask and the first prior image, and the second projection dataset based on the second metal mask and the second prior image; and blending the first interpolated projection dataset with the first projection dataset to generate the first metal-reduced projection dataset, and the second interpolated projection dataset with the second projection dataset to generate the second metal-reduced projection dataset.

In one example, generating the second metal mask based on the first metal mask and the second projection dataset comprises selecting values of the second projection dataset based on the first metal mask.

As another example, generating the second prior image based on at least the first prior image comprises transforming the values of the first prior image to form the second prior image.

In yet another example, the first interpolated projection dataset and the first projection dataset are blended using a weighting function, the weighting function calculated based on the first projection dataset and the first metal mask, and wherein the second interpolated projection dataset and the second projection dataset are blended using the weighting function.

In one example, generating the first metal image and the second metal image based on the first material image and the second material image comprises: generating a mono-energetic image based on the first material image and the second material image; generating a binary metal mask by thresholding the mono-energetic image with a metal threshold calculated based on the first projection dataset; and generating the first metal image by multiplying the first material image with the binary metal mask, and the second metal image by multiplying the second material image with the binary metal mask.

In some examples, the first projection dataset comprises a higher energy projection dataset and the second projection dataset comprises a lower energy projection dataset.

In yet another embodiment, an imaging system comprises: an x-ray source that emits a beam of x-rays toward an object to be imaged, the x-ray source configured to emit x-rays with a high energy and a low energy; a detector that receives the x-rays attenuated by the object; and a data acquisition system (DAS) operably connected to the detector. The imaging system further comprises a computer operably connected to the DAS and programmed with instructions in non-transitory memory that when executed cause the computer to acquire, via the DAS, a first projection dataset and a second projection dataset, detect a location of metal in the first projection dataset, generate a first metal-corrected projection dataset based on the first projection dataset and the location of the metal, and generate a second metal-corrected projection dataset based on the second projection dataset and the location of the metal.

In one example, the system further comprises a display, and the computer is further programmed with instructions in the non-transitory memory that when executed cause the computer to output an image to the display, the image reconstructed based on the first metal-corrected projection dataset and the second metal-corrected projection dataset.

Note that the example control routines included herein can be used with various imaging system configurations. The routines and methods disclosed herein may be stored as executable instructions in non-transitory memory and may be carried out by the imaging system including the computer in combination with the various system components, such as the detector assembly, the operator console, and so on.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   acquiring a first projection dataset and a second projection dataset;
   detecting a location of metal in the first projection dataset based on a metal threshold;
   applying corrections to the first and second projection datasets based on the location of the metal; and
   displaying an image reconstructed from the corrected first and second projection datasets.

2. The method of claim 1, wherein detecting the location of the metal in the first projection dataset comprises generating a first metal mask comprising voxels above the metal threshold in a first backprojection of the first projection dataset.

3. The method of claim 2, further comprising generating a second metal mask comprising voxels in a second backprojection of the second projection dataset at a same location of the voxels in the first metal mask.

4. The method of claim 1, further comprising generating a first prior image based on the first projection dataset and the location of the metal, and generating a second prior image based on the second projection dataset and the first prior image.

5. The method of claim 4, further comprising segmenting the first prior image into at least two regions based on selected threshold values.

6. The method of claim 5, wherein generating the second prior image based on the first prior image comprises generating the second prior image based on the segmentation of the first prior image.

7. The method of claim 4, wherein generating the second prior image based on the first prior image comprises transforming pixel values of the first prior image based on an acquisition energy of the second projection dataset.

8. The method of claim 4, wherein applying the corrections comprises generating a first interpolated projection dataset based on a forward projection of the first prior image, and generating a second interpolated projection dataset based on a forward projection of the second prior image.

9. The method of claim 8, wherein applying the corrections further comprises:
   calculating a weighting function based on the first projection dataset and the location of the metal;
   blending the first interpolated projection dataset with the first projection dataset based on the weighting function; and
   blending the second interpolated projection dataset with the second projection dataset based on the weighting function.

10. The method of claim 1, further comprising generating a first metal image and a second metal image based on the metal threshold.

11. The method of claim 1, wherein the first projection dataset comprises a higher energy projection dataset and the second projection dataset comprises a lower energy projection dataset.

12. A method, comprising:
    acquiring a first projection dataset and a second projection dataset;
    generating a first metal-reduced projection dataset based on the first projection dataset and a second metal-reduced projection dataset based on the second projection dataset and the first projection dataset;
    decomposing the first and the second metal-reduced projection datasets into a first metal-reduced material basis and a second metal-reduced material basis, and the first and the second projection datasets into a first material basis and a second material basis;
    reconstructing a first metal-reduced material image based on the first metal-reduced material basis, a second metal-reduced material image based on the second metal-reduced material basis, a first material image based on the first material basis, and a second material image based on the second material basis;
    generating a first metal image and a second metal image based on the first material image and the second material image;
    generating a first metal-corrected image by combining the first metal image and the first metal-reduced material image;
    generating a second metal-corrected image by combining the second metal image and the second metal-reduced material image; and
    outputting at least one of the first metal-corrected image, the second metal-corrected image, and a mono-energetic image comprising a combination of the first metal-corrected image and the second metal-corrected image.

13. The method of claim 12, wherein generating the first metal-reduced projection dataset and the second metal-reduced projection dataset comprises:
    generating a first metal mask based on the first projection dataset, and a second metal mask based on the first metal mask and the second projection dataset;
    generating a first prior image based on the first projection dataset and the first metal mask, and a second prior image based on the first prior image;
    interpolating the first projection dataset based on the first metal mask and the first prior image, and the second projection dataset based on the second metal mask and the second prior image; and
    blending the first interpolated projection dataset with the first projection dataset to generate the first metal-reduced projection dataset, and the second interpolated projection dataset with the second projection dataset to generate the second metal-reduced projection dataset.

14. The method of claim 13, wherein generating the second metal mask based on the first metal mask and the second projection dataset comprises selecting values of the second projection dataset based on the first metal mask.

15. The method of claim 13, wherein generating the second prior image based on at least the first prior image comprises transforming the values of the first prior image to form the second prior image.

16. The method of claim 13, wherein the first interpolated projection dataset and the first projection dataset are blended using a weighting function, the weighting function calculated based on the first projection dataset and the first metal mask, and wherein the second interpolated projection dataset and the second projection dataset are blended using the weighting function.

17. The method of claim 13, wherein generating the first metal image and the second metal image based on the first material image and the second material image comprises:
generating a mono-energetic image based on the first material image and the second material image;
generating a binary metal mask by thresholding the mono-energetic image with a metal threshold calculated based on the first projection dataset; and
generating the first metal image by multiplying the first material image with the binary metal mask, and the second metal image by multiplying the second material image with the binary metal mask.

18. The method of claim 12, wherein the first projection dataset comprises a higher energy projection dataset and the second projection dataset comprises a lower energy projection dataset.

19. An imaging system, comprising:
an x-ray source that emits a beam of x-rays toward an object to be imaged, the x-ray source configured to emit x-rays with a high energy and a low energy;
a detector that receives the x-rays attenuated by the object;
a data acquisition system (DAS) operably connected to the detector; and
a computer operably connected to the DAS and programmed with instructions in non-transitory memory that when executed cause the computer to:
acquire, via the DAS, a first projection dataset and a second projection dataset;
detect a location of metal in the first projection dataset;
generate a first metal-corrected projection dataset based on the first projection dataset and the location of the metal; and
generate a second metal-corrected projection dataset based on the second projection dataset and the location of the metal.

20. The system of claim 19, further comprising a display, and wherein the computer is further programmed with instructions in the non-transitory memory that when executed cause the computer to output an image to the display, the image reconstructed based on the first metal-corrected projection dataset and the second metal-corrected projection dataset.

* * * * *